(12) United States Patent
Novak et al.

(10) Patent No.: US 7,931,611 B2
(45) Date of Patent: Apr. 26, 2011

(54) ULTRASONIC WOUND DEBRIDER PROBE AND METHOD OF USE

(75) Inventors: Theodore A. D. Novak, Northport, NY (US); Ronald R. Manna, Valley Stream, NY (US); Dan Voic, Clifton, NJ (US); Scott Isola, Deer Park, NY (US)

(73) Assignee: Misonix, Incorporated, Farmingdale, NY (US)

( * ) Notice: Subject to any disclaimer, the term of this patent is extended or adjusted under 35 U.S.C. 154(b) by 937 days.

(21) Appl. No.: 11/087,451

(22) Filed: Mar. 23, 2005

(65) Prior Publication Data

US 2006/0241470 A1 Oct. 26, 2006

(51) Int. Cl.
*A61B 17/20* (2006.01)
(52) U.S. Cl. .......................... 604/22; 264/442
(58) Field of Classification Search .............. 604/22; 128/200.16; 156/580.1, 580.2, 73.1; 178/18.04; 204/157.42, 157.62; 219/706; 228/110.1; 264/407, 442
See application file for complete search history.

(56) References Cited

U.S. PATENT DOCUMENTS

| | | | |
|---|---|---|---|
| 3,937,236 A | 2/1976 | Runnells | |
| 4,223,676 A | 9/1980 | Wuchinich et al. | |
| 4,872,353 A | 10/1989 | Orr et al. | |
| 4,874,137 A | 10/1989 | Chiba | |
| 4,930,532 A | 6/1990 | Mayer | |
| 4,989,583 A * | 2/1991 | Hood | 601/2 |
| 5,095,188 A | 3/1992 | Klein | |
| 5,112,300 A * | 5/1992 | Ureche | 604/22 |
| 5,167,231 A | 12/1992 | Matsui | |
| 5,171,387 A | 12/1992 | Wuchinich | |
| 5,180,363 A * | 1/1993 | Idemoto et al. | 604/22 |
| 5,185,728 A | 2/1993 | Gilchrist | |
| 5,188,102 A | 2/1993 | Idemoto et al. | |
| 5,459,699 A | 10/1995 | Walter | |
| 5,512,335 A | 4/1996 | Miller et al. | |

(Continued)

FOREIGN PATENT DOCUMENTS

EP 0943405 9/1999

(Continued)

OTHER PUBLICATIONS

"One-Step Microplate Sonication: Misonix 431-T Tray Horn"; The Scientist 13(12):14, Jun. 7, 1999.

*Primary Examiner* — Nicholas D Lucchesi
*Assistant Examiner* — Gerald Landry, II
(74) *Attorney, Agent, or Firm* — R. Neil Sudol; Henry D. Coleman; William J. Sapone

(57) ABSTRACT

An ultrasonic medical probe comprises an elongate shaft formed integrally with a head portion having a distal end face oriented at least partially transversely to a longitudinal axis of the shaft. The shaft is provided with an internal longitudinal channel or bore extending to the end face. The end face is formed with an indentation communicating with the channel or bore at a distal end thereof, whereby liquid is guided over an extended surface of the end face relative to the channel or bore. The head portion also has a lateral surface extending substantially parallel to the longitudinal axis of the probe. The lateral surface is provided with at least one outwardly or radially extending projection. The projection enables the application of ultrasonic cavitation energy to a tissue surface that is in contact with the lateral or side surface of the probe head.

30 Claims, 2 Drawing Sheets

U.S. PATENT DOCUMENTS

| | | | |
|---|---|---|---|
| 5,779,985 A | 7/1998 | Sucholeiki | |
| 5,931,847 A * | 8/1999 | Bittner et al. | 606/167 |
| 5,951,546 A * | 9/1999 | Lorentzen | 606/41 |
| 6,027,009 A | 2/2000 | Shinchi | |
| 6,071,480 A | 6/2000 | Halaka | |
| 6,152,383 A | 11/2000 | Chen | |
| 6,277,332 B1 | 8/2001 | Sucholeiki | |
| 6,578,659 B2 | 6/2003 | Manna et al. | |
| 7,611,473 B2 * | 11/2009 | Boock et al. | 600/564 |
| 2003/0023193 A1 | 1/2003 | Soring et al. | |
| 2003/0176791 A1 * | 9/2003 | Rabiner et al. | 600/439 |
| 2003/0187383 A1 * | 10/2003 | Weber et al. | 604/22 |
| 2003/0203491 A1 | 10/2003 | Andrevski et al. | |
| 2004/0030254 A1 | 2/2004 | Babaev | |
| 2004/0030349 A1 * | 2/2004 | Boukhny | 606/166 |
| 2005/0177184 A1 * | 8/2005 | Easley | 606/167 |

FOREIGN PATENT DOCUMENTS

| | | |
|---|---|---|
| EP | 1101577 | 5/2001 |
| JP | 62282914 | 12/1987 |
| JP | 9222424 | 8/1997 |

* cited by examiner

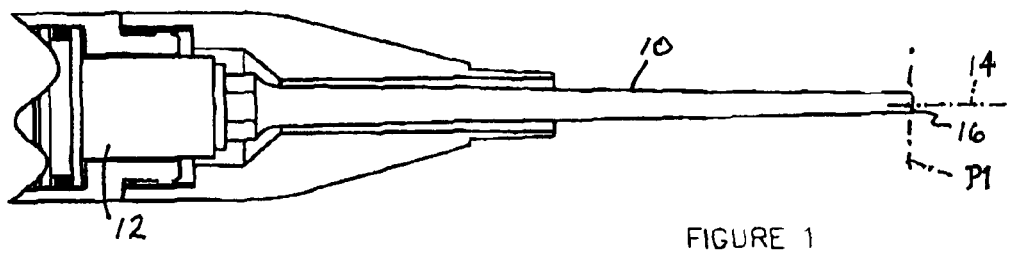
FIGURE 1
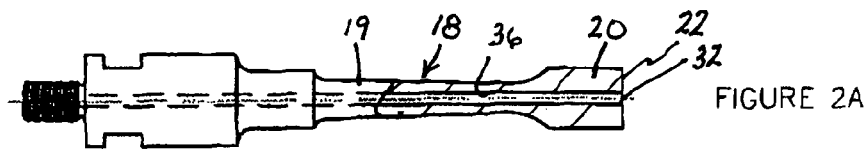
FIGURE 2A
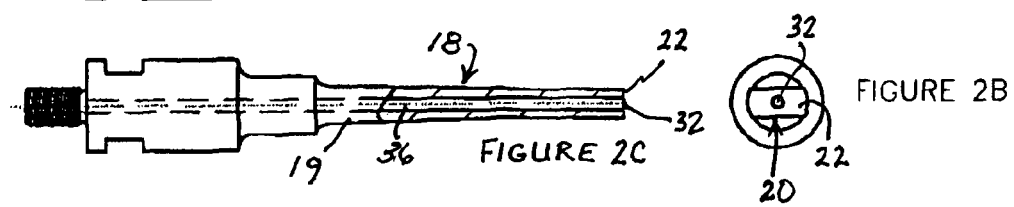
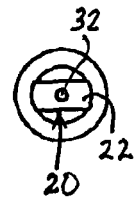
FIGURE 2B
FIGURE 2C
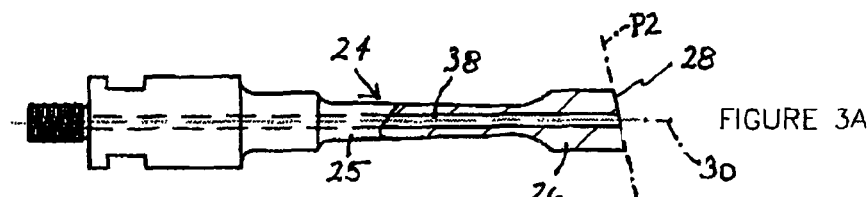
FIGURE 3A
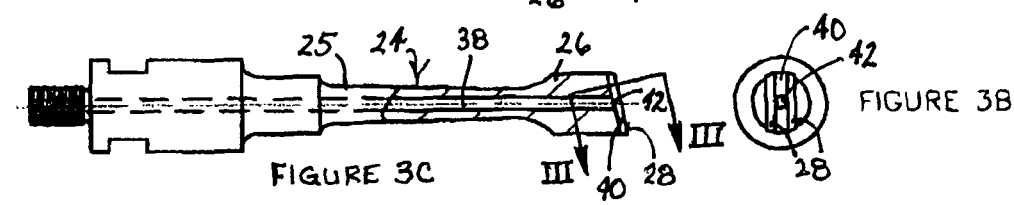
FIGURE 3B
FIGURE 3C
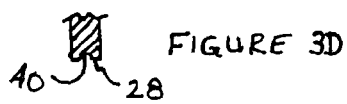
FIGURE 3D
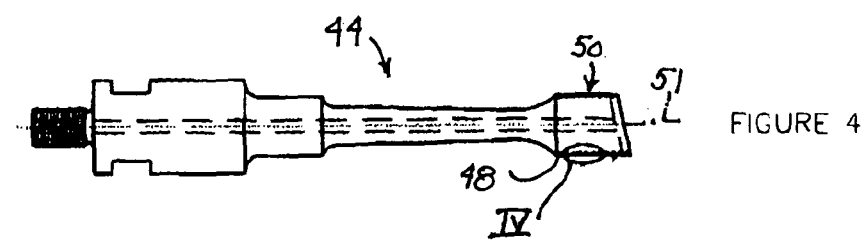
FIGURE 4
FIGURE 4A

ULTRASONIC WOUND DEBRIDER PROBE AND METHOD OF USE

BACKGROUND OF THE INVENTION

This invention relates to ultrasonic surgical instruments and associated methods of use. More particularly, this invention relates to high-efficiency medical treatment probes for ultrasonic surgical aspirators. These probes increase the ability to fragment and emulsify hard and soft tissue in a clinical environment while reducing unwanted heat and collateral tissue damage.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, tissue compression and relaxation stresses (sometimes called the jackhammer effect) or by other forces such as micro streaming of bubbles in the tissue matrix. The effect is that the tissue becomes liquefied and separated. It then becomes emulsified with the irrigant solution. The resulting emulsion is then aspirated from the site. Bulk excision of tissue is possible by applying the energy around and under an unwanted tumor to separate it from the surrounding structure. The surgeon can then lift the tissue out using common tools such as forceps.

The probe or tube is excited by a transducer of either the piezoelectric or magnetostrictive type that transforms an alternating electrical signal within the frequencies indicated into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis, as shown in FIG. 1. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

Therefore, it is desired to provide a probe that can be mated to an ultrasonic surgical aspirator which increases the efficiency of emulsification, does not heat up the operative site and lowers the time of operation.

OBJECTS OF THE INVENTION

An object of the present invention is to provide an improved ultrasonic surgical instrument for use in debridement of wounds.

A more particular object of the present invention is to provide such an instrument in the form of a probe that may be used in conjunction with ultrasonic surgical aspirators to debride wounds.

Another relatively specific object of the present invention is to provide an improved ultrasonic surgical instrument with a form that enhances surgical efficiency and reduces the time required to complete at least some kinds of debridement procedures.

It is a further object of the present invention to provide such an improved ultrasonic surgical instrument with irrigation or suction capability.

It is an additional object of the present invention to provide an improved ultrasonic surgical instrument that may be used in debriding deep wounds such as cuts and puncture wounds.

An additional object of the present invention is to provide an improved ultrasonic surgical instrument that has liquid directing channels for greater heat reduction at the distal face and to prevent liquid jetting or spraying from the tissue probe interface.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A probe for use as an ultrasonically vibrating tool is disclosed with a central bore coincident with the longitudinal axis. The proximal end of said bore communicates with a bore in the ultrasonic handpiece using methods well known to the art, such as a male/female thread combination. The probe is shaped such as to provide both a resonant frequency of operation in the range for which the electronic generator was designed and an amplitude of vibration at the distal face which is desired for proper tissue ablation. Such amplitudes have generally been shown to be in the range of 30 to 300 microns. Again, the technique needed for calculating said shapes is well known to the art and outside the scope of this disclosure.

Probe heads or ends in accordance with the present invention incorporate either a substantially symmetrical distal end or a distal end with a pronounced asymmetry. Each end has attributes that increase its effectiveness on varying tissue pathologies.

Probe ends pursuant to the present invention are further modified to improve the liquid flow to the probe/tissue interface such as to reduce the bulk temperature rise of the tissue and prevent clogging of the liquid passageway. Probe ends are further modified to produce energy directors that impart energy from the sides of the probes instead of only at the distal face of the probe. Such energy directors, when contacting skin or tissue, will increase volume of tissue treated per unit time and thereby reduce the operating time of the procedure.

In one embodiment of the present invention, an ultrasonic medical probe comprises an elongate shaft formed integrally with a head portion having a distal end face oriented at least partially transversely to a longitudinal axis of the shaft. The shaft is provided with an internal longitudinal channel or bore extending to the end face. The end face is formed with an indentation communicating with the channel or bore at a distal end thereof, whereby liquid is guided over an extended surface of the end face relative to the channel or bore.

The head portion may be enlarged in a transverse direction relative to the shaft. In that event, the end face has an elongated shape, while the indentation is elongate and forms a groove in the end face of the head portion. This groove may extend parallel to or in a length dimension of the end face.

When the channel or bore is connected to a suction source, fluid in the indentation flows toward the channel or bore. When the channel or bore is connected to a source of irrigation liquid, liquid in the indentation flows away from the channel or bore.

Pursuant to a feature of the present invention, the end face is inclined or beveled relative to the longitudinal axis of the probe.

In another embodiment of the present invention, an ultrasonic medical probe comprises an elongate shaft formed integrally with a head portion having a distal end face oriented at least partially transversely to a longitudinal axis of the shaft. The head portion also has a lateral surface extending substantially parallel to the longitudinal axis of the probe. The lateral surface is provided with at least one outwardly or radially extending projection. The projection enables the application of ultrasonic cavitation energy to a tissue surface that is in contact with the lateral or side surface of the probe head.

Pursuant to a feature of the present invention, the projection is one of a plurality of projections extending from the lateral surface. The projections may be identical to one another and staggered from one another along the lateral surface of the probe head. The projections may have a shape that is pyramidal, semi-cylindrical, wedge-shaped, or plate-like. The projections may lie down against the lateral surface of the probe head, in the nature of fish scales, flaps, or flattened plates.

The projections may take the form of ridges. The projections or ridges may extend perimetrally or circumferentially about the probe head. Preferably, however, the projections or ridges are disposed only along one side (or possibly two sides, in some applications) of the probe head. The probe head may take a prismatic form, with the energy-directing projections or ridges formed along one (or two) lateral surfaces thereof. This placement of the energy-directing projections facilitates use of the probe in surgical procedures, inasmuch as it is easier for the surgeon to keep track of the location of the projections to ensure that the projections come into contact only with target debridement tissues.

It is contemplated that the projections may be finely distributed over a lateral face of the probe head so as to form a knurled surface. Such a knurled surface is similar to that found on a metal filing tool.

As discussed above, the shaft and the probe head may be provided with an internal longitudinal channel or bore extending to the end face of the probe head, with the end face being formed with an indentation communicating with the channel or bore at a distal end thereof. The indentation extends laterally relative to the channel or bore, whereby liquid is guided over an extended surface of the end face relative to the channel or bore.

The indentation may be elongate and form a groove in the end face of the head portion. Where the head portion has an elongated shape, the groove may extend parallel to a length dimension of the end face.

A surgical method in accordance with the present invention utilizes a probe vibratable at at least one ultrasonic frequency, the probe having a distal end face oriented at least partially transversely to a longitudinal axis of the shaft. The method comprises bringing the distal end face into contact with organic tissues of a patient, energizing the probe to vibrate the end face at the ultrasonic frequency during the contacting of the tissues with the distal end face, and channeling liquid between the contacted tissues and a longitudinal bore in the probe, during the contacting of the tissues with the distal end face, via an indentation in the end face communicating with the bore.

Where the bore is connected to a suction source, the channeling of liquid includes guiding liquid from the contacted tissues to the bore.

Where the bore is connected to a source of irrigation liquid, the channeling of liquid comprises guiding liquid to the contacted tissues from the bore.

A surgical method in accordance with another feature of the present invention utilizes a probe vibratable at at least one ultrasonic frequency, where the probe has a distal end face oriented at least partially transversely to a longitudinal axis of the shaft, a lateral surface extending substantially perpendicularly to the end face and substantially parallel to the longitudinal axis, and at least one outwardly or radially extending projection extending out from the lateral surface. The method comprises bringing the lateral surface together with the projection into contact with organic tissues of a patient and, during the contacting of the tissues with the lateral surface and the projection, energizing the probe to vibrate the lateral surface and the projection at the ultrasonic frequency.

Pursuant to another feature of the present invention, the bringing of the lateral surface together with the projection into contact with organic tissues of a patient includes inserting a distal end portion of the probe into a fissure or recess in an organ of the patient and moving the probe so that the lateral surface and the projection contact a wall of the fissure or recess.

According to another feature of the present invention, the bringing the lateral surface together with the projection into contact with organic tissues of a patient includes manipulating the probe so that the lateral surface is oriented substantially parallel to the organic tissues and so that the end face is oriented substantially perpendicularly to the organic tissues immediately prior to an engaging of the organic tissues with the lateral surface and the projection. In one embodiment of the present invention, an ultrasonic medical probe comprises an elongate shaft formed integrally with a head portion having a distal end face oriented at least partially transversely to a longitudinal axis of the shaft. The shaft is provided with an internal longitudinal channel or bore extending to the end face. The end face is formed with an indentation communicating with the channel or bore at a distal end thereof, whereby liquid is guided over an extended surface of the end face relative to the channel or bore.

The head portion may be enlarged in a transverse direction relative to the shaft. In that event, the end face has an elongated shape, while the indentation is elongate and forms a groove in the end face of the head portion. This groove may extend parallel to or in a length dimension of the end face.

When the channel or bore is connected to a suction source, fluid in the indentation flows toward the channel or bore. When the channel or bore is connected to a source of irrigation liquid, liquid in the indentation flows away from the channel or bore.

Pursuant to a feature of the present invention, the end face is inclined or beveled relative to the longitudinal axis of the probe.

In another embodiment of the present invention, an ultrasonic medical probe comprises an elongate shaft formed integrally with a head portion having a distal end face oriented at least partially transversely to a longitudinal axis of the shaft. The head portion also has a lateral surface extending substantially parallel to the longitudinal axis of the probe. The lateral surface is provided with at least one outwardly or radially extending projection. The projection enables the application of ultrasonic cavitation energy to a tissue surface that is in contact with the lateral or side surface of the probe head.

Pursuant to a feature of the present invention, the projection is one of a plurality of projections extending from the lateral surface. The projections may be identical to one another and staggered from one another along the lateral surface of the probe head. The projections may have a shape that is pyramidal, semi-cylindrical, wedge-shaped, or plate-like. The projections may lie down against the lateral surface of the probe head, in the nature of fish scales, flaps, or flattened plates.

The projections may take the form of ridges or knurls. Preferably, the projections are disposed along only a portion of the lateral surface area of the probe head. For example, where the probe head is prismatic with three or more planar lateral faces, the energy-direting projections are disposed along less than all of the lateral faces of the probe head. More preferably, the projections are disposed along only one or two lateral faces of the probe head.

As discussed above, the shaft and the probe head may be provided with an internal longitudinal channel or bore extending to the end face of the probe head, with the end face being formed with an indentation communicating with the channel or bore at a distal end thereof. The indentation extends laterally relative to the channel or bore, whereby liquid is guided over an extended surface of the end face relative to the channel or bore.

The indentation may be elongate and form a groove in the end face of the head portion. Where the head portion has an elongated shape, the groove may extend parallel to a length dimension of the end face.

A surgical method in accordance with the present invention utilizes a probe vibratable at at least one ultrasonic frequency, the probe having a distal end face oriented at least partially transversely to a longitudinal axis of the shaft. The method comprises bringing the distal end face into contact with organic tissues of a patient, energizing the probe to vibrate the end face at the ultrasonic frequency during the contacting of the tissues with the distal end face, and channeling liquid between the contacted tissues and a longitudinal bore in the probe, during the contacting of the tissues with the distal end face, via an indentation in the end face communicating with the bore.

Where the bore is connected to a suction source, the channeling of liquid includes guiding liquid from the contacted tissues to the bore.

Where the bore is connected to a source of irrigation liquid, the channeling of liquid comprises guiding liquid to the contacted tissues from the bore.

A surgical method in accordance with another feature of the present invention utilizes a probe vibratable at at least one ultrasonic frequency, where the probe has a distal end face oriented at least partially transversely to a longitudinal axis of the shaft, a lateral surface extending substantially perpendicularly to the end face and substantially parallel to the longitudinal axis, and at least one outwardly or radially extending projection extending out from the lateral surface. The method comprises bringing the lateral surface together with the projection into contact with organic tissues of a patient and, during the contacting of the tissues with the lateral surface and the projection, energizing the probe to vibrate the lateral surface and the projection at the ultrasonic frequency.

Pursuant to another feature of the present invention, the bringing of the lateral surface together with the projection into contact with organic tissues of a patient includes inserting a distal end portion of the probe into a fissure or recess in an organ of the patient and moving the probe so that the lateral surface and the projection contact a wall of the fissure or recess. According to another feature of the present invention, the bringing the lateral surface together with the projection into contact with organic tissues of a patient includes manipulating the probe so that the lateral surface is oriented substantially parallel to the organic tissues and so that the end face is oriented substantially perpendicularly to the organic tissues immediately prior to an engaging of the organic tissues with the lateral surface and the projection.

BRIEF DESCRIPTION OF THE DRAWINGS

FIG. 1 is a cross sectional view of a prior art ultrasonic probe for use with an ultrasonic aspirator.

FIG. 2A is partially a side elevational view and partially a cross-sectional view of an ultrasonic probe in accordance with the present invention.

FIG. 2B is a distal end elevational view of the probe of FIG. 2A.

FIG. 2C is partially a top elevational view and partially a cross-sectional view of the probe of FIG. 2A.

FIG. 3A is partially a side elevational view and partially a cross-sectional view of another ultrasonic probe in accordance with the present invention.

FIG. 3B is a distal end elevational view of the probe of FIG. 3A, showing a modification in the form of an elongate groove in a distal end face of the probe head.

FIG. 3C is a view similar to FIG. 3A showing the groove of FIG. 3B.

FIG. 3D is a partial cross-sectional view taken along line III-III in FIG. 3C.

FIG. 4 is partially a side elevational view and partially a cross-sectional view of a further ultrasonic probe in accordance with the present invention.

FIG. 4A is partial view, on a larger scale, of a lateral surface of a head of the probe of FIG. 4, taken in region IV-IV of FIG. 4.

DETAILED DESCRIPTION

Figure 4B:
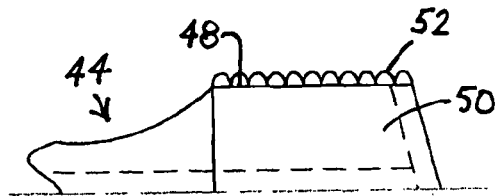
FIGS. 4B-4D are side elevational views of the probe head of FIG. 4, showing respective modifications of formations along the lateral surface thereof.
Figure 4C:
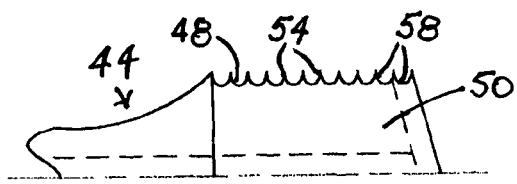
Figure 4D:
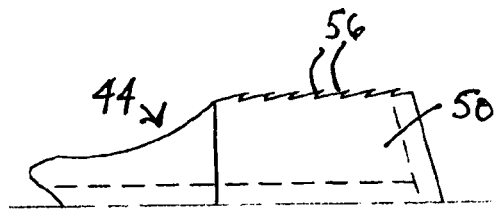
Figure 4E:
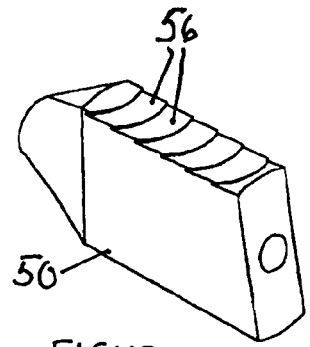
FIG. 4E is a perspective view of the probe head depicted in FIG. 4D.

Several probes are disclosed which embody the improvements described herein. FIG. 1 shows a probe 10 which is known to the art and is currently manufactured for use with an ultrasonic aspirator. This probe 10 is basically shaped with an exponential or Gaussian taper. Probe 10 is cannulated and has an integral male thread (not shown) at the proximal end (proximate the operator). This thread communicates with a female threaded bore (not illustrated) in the transducer 12. By tightening the probe 10 onto the transducer 12 and using standard wrenches for final torquing, the transducer and probe essentially become one resonant body. Bores of the probe 10 and transducer 12 communicate with one another. The probe 10 is generally constructed of an acoustically efficient metal or ceramic. Titanium is the most commonly used material, but other material has been employed with success. Material choice does not have a significant impact upon the embodiments of this disclosure.

The distal end of the prior art probe 10 is truncated in a plane P1 perpendicular to the longitudinal axis 14 of the resonant body (probe and transducer). Since the probe 10 is cannulated, a distal end face 16 takes the form of an annular surface with a small cross sectional area. The shape of the probe 10 allows the probe to become a velocity transformer, i.e., the probe will amplify the input vibrations from the transducer 12 by a fixed value, called a gain factor, determined by the geometry of the probe. For example, if the probe 10 had a gain factor of 10, the probe would multiply the input vibration of the transducer, for example 30 microns, to a final amplitude at the distal end of the probe of 300 microns. This phenomenon is well known to the art. By placing the distal end face 16 of probe 10 against organic tissue of a patient, the tissue will be disrupted through cavitation and mechanical effects. By adding saline or water to the tissue-probe interface, cooling of the tissue is achieved and the tissue is emulsified into the liquid and is more easily aspirated either through the center of the probe 10, if the center bore is connected to the aspirator or by separate suction cannulae if the center bore is connected to the irrigant source.

However, the distal end of probe 10 in its conventional configuration is not conducive to ablating large volumes of tissue in short periods of time. By increasing the surface area of distal end face 16, a probe can be constructed which will ablate tissue faster and allow for a shorter operation. This is especially advantageous when debriding wounds such as bedsores, diabetic ulcers, burn wounds, etc.

FIGS. 2A-2C show a probe 18 with a shaft 19 and an enlarged distal head 20. More particularly, probe head 20 may be asymmetrical such that the cross sectional shape is rectangular or oval (see FIG. 2B). This asymmetry allows the probe 18 to maintain a higher gain factor and be more able to be inserted into smaller wounds. The surface area of a distal end face 22 of probe head 20 is greatly increased over the prior art probe (FIG. 1) and will naturally ablate tissue at a higher rate. The shape of the probe head 20 allows access to irregularly shaped wound beds, such as cuts or fissures with slit openings.

Although the probe of FIGS. 2A-2C has been shown to have higher performance over prior art, further improvements may be made. FIG. 3A depicts a probe 24 having a shaft 25 and an asymmetrically enlarged head 26 with a truncated or beveled distal end face 28 located in a plane P2 that is not perpendicular to a longitudinal axis 30 of the probe. This probe 24 has been shown to improve performance in removing the hard eschar buildup of burn wounds, which must be removed in order to expose healthy tissue.

One problem that is encountered in such probe designs, whether the probe head is truncated in a perpendicular plane P1 such as head 20 or in a plane P2 inclined relative to the instrument axis 30 such as probe head 26, is the bore opening 32 or 34 may become blocked with tissue. This blockage prevents aspiration of the emulsified tissue, if the respective bore 36 or 38 is connected to a vacuum source (not shown) or blocks the flow of cooling fluid out of the probe, if the bore is attached to a pressurized liquid source (not shown). Because of the pressure buildup, the liquid has a tendency to jet or stream from the probe tissue interface, causing the irrigant to be sprayed around the room instead of onto the wound bed. Also, if the distal end face of the probe is very large, the liquid may not cover the entire face, even if the opening 32, 34 at the end of the probe is not blocked.

In order to improve the performance of the probe 24 in this regard, a channel, recess, groove, indentation, or notch 40 is provided in the end face 28 of the probe, as shown in FIGS. 3B, 3C and 3D. Bore 38 extends to this recess, groove, indentation or notch 40, with the outlet opening 32 of the channel or bore being located therein. Channel 40 extends inwardly from face 28 and is defined by at least two peripheral edges formed at respective junctions with the probe end face (see vertical lines flanking channel 40 in FIG. 3B). Channel 40 has a radius of curvature (see FIG. 3D) substantially smaller than any radius of curvature of probe end face 28. This channel 40 reduces the likelihood of blockage of an output opening 42 of the probe bore 38 by locating this opening or outlet proximally from the distal end face 28 of the probe head 26, while allowing the liquid to fill the channel 40, to flow along the channel and from the indentation to cover the remaining distal surface area more fully. Many alternative shapes of channels may be employed in the distal end faces of ultrasonic probes without changing the concepts outlined herein. In the illustrated example, channel or groove 40 extends parallel to or in a length dimension of the end face 28.

When bore 38 is connected to a suction source (not shown), fluid in the channel 40 flows toward the bore 38. When the channel or bore 38 is connected to a source of irrigation liquid (not shown), liquid in the channel 40 flows away from the bore 38.

Regardless of the shape of the distal surface or end faces of the probes as discussed hereinabove, the probes are limited in their ability to ablate tissue by the fact the only area where this ablation can occur is at the distal end face. The sides or lateral surfaces of the probes are generally disposed parallel to the longitudinal axes and parallel to the direction of ultrasonic compression wave transmission. When tissue touches these lateral surfaces, no ablation occurs since the motion is a sliding or rubbing action, which does not transmit sufficient energy into the tissue to cause emulsion or ablation. It is therefore desired to improve ultrasonic tissue ablation probes so that energy may be transmitted from one or more lateral faces or side surfaces of the probe heads so that more tissue may be ablated per unit time.

FIGS. 4 and 4A show a probe 44 which is identical to probe 24 of FIGS. 3B-3D with the addition of outwardly or radially extending projections 46 serving as energy guides or directors disposed along at least one lateral or side surface 48 of a probe head 50. Preferably, probe head 50 has a prismatic shape with four planar lateral surfaces or faces 48, projections 46 being disposed only along one or two of the lateral surfaces. As depicted in FIG. 4, energy-directing projections 46 are disposed only along two opposing lateral surfaces 48. Where projections occur along only one or at most two lateral surfaces 48, it is easier for the user to avoid contact with non-target tissues.

Probe head 50 may be integrally formed with a shaft portion 49 of probe 44. Alternatively, probe head 50 may be formed as a separate piece that is firmly attached to shaft 49, e.g., via mating screw threads (not shown) or a force or friction fit. These same alternatives also apply to probe heads 20, 26, 66.

Projections 46 may have a fine geometrical configuration and distribution so as to form the respective lateral surface 48 into a knurled surface as one would find, for example, on a metal file. Or projections 46 may be a series of ridges or knurls on probe head 50. Alternatively, as shown in FIG. 4B, projections or energy directors 46 may be pyramidal sections fashioned from the base metal of the probe 44 that project out in a substantially perpendicular direction from a longitudinal axis 51 of the probe. More specifically, projections or energy directors 46 are a series of parallel ridges or knurls each of triangular cross-section extending transversely to a direction of ultrasonic wave propagation. Projections or energy directors 46 may include a first set of parallel ridges 46a and a second set of ridges 46b that is staggered relative to the first set. Each set of wedge- or triangle-shaped projections or ridges 46a, 46b defines a corresponding set of grooves (not separately designated) each of triangular cross-section extending transversely to a direction of ultrasonic wave propagation. The resulting faceted surfaces of projections or ridges 46a, 46b impart a vector force on the target tissue when the probe 44 vibrates, which will cause cavitation and emulsification of the tissue when it contacts the faceted surfaces.

As illustrated in FIGS. 4B-4E, lateral surface 48 may be provided with energy-directing projections or ridges 52, 54, 56 of different geometrical shapes. Projections or ridges 52 are convex, for instance, semi-cylindrical. Projections or ridges 54 define concave grooves or recesses 58. Projections 56 are flattened plates or flaps that lie against lateral surface 48 in the natural of fish scales. These energy directors or projections 52, 54, 56 allow faster tissue ablation by creating a much larger active surface area at the distal end of the probe 44.

Figure 5:
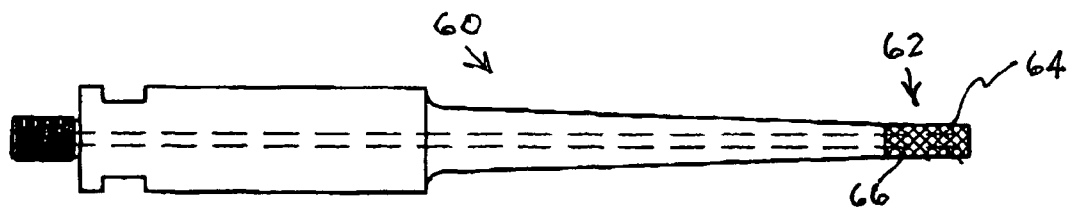
FIG. 5 is partially a side elevational view and partially a cross-sectional view of yet another ultrasonic probe in accordance with the present invention.

In cases where a probe tip must be smaller than that allowed by the described embodiment, such as when small and/or deep bedsores or wounds must be debrided, the probe tip may be improved to allow faster ablation as well. FIG. 5 shows a probe 60 in the configuration of a tubular end or head 62. Probe 60 is provided circumferentially along a cylindrical lateral or side surface 64 or probe head 62 with a plurality of pyramidal energy-directing projections 66. Projections 66 may be small such as that which occurs in a knurled surface, for example, on a metal file. The energy directors 66 will impart vector forces on the tissue when in contact with the wound bed such that emulsion and ablation will occur around the probe as well as in front of it. Such probes have been shown to increase the speed of ablation and thereby significantly reduce the time of operation. Again, such energy directors may be purely pyramidal, or have concave or convex faces.

All said probes in this embodiment might be designed by those skilled in the art using known tools and techniques.

In a method of using the above-described probes for debriding and cleaning wounds, sores and ulcers with ultrasound energy, an operator assembles the ultrasonic surgical aspirator with the probes, connects the central bore to a pressurized liquid source which can be adjusted to provide a controlled flow at the probe tip, turn on the system to provide between 30 and 350 microns of probe tip displacement, and touches the tip and the energy directors to the tissue to be ablated, causing cavitational and mechanical forces to be imparted to said tissue which ablates the tissue, thereby debriding and cleansing the wound bed. Aspiration may be accomplished simultaneously or separately from ultrasonic ablation by connecting a flue or sheath around said probe, as in FIG. 6, that is in turn connected to a vacuum source and then the emulsified tissue is aspirated through this annular space. Conversely, the flue or sheath may be eliminated and the aspirate removed via separate suction cannulae.

A surgical method utilizing probe 24 or 44 or another probe provided in an end face with a channel, groove, indentation, or notch such as channel 40 is operated to vibrate at an ultrasonic frequency. The distal end face 22, 28 of the probe is brought into contact with organic tissues of a patient. The probe is energized to ultrasonically vibrate the end face 22, 28 during the contacting of the tissues with the distal end face, and liquid is channeled between the contacted tissues and longitudinal bore 36, 38, during the contacting of the tissues with the distal end face, via indentation or channel 40.

A surgical method utilizing probe 44 or 60 comprises bringing the lateral surface 48 or 64 together with projections, ridges, or knurls 46, 66 into contact with organic tissues of a patient and, during the contacting of the tissues with the lateral surface and the projections, energizing the probe to vibrate the lateral surface 48, 64 and the projections 46, 66 at a predetermined ultrasonic frequency. This method may include inserting a distal end portion of the probe into a cut, fissure or recess in an organ of the patient and moving the probe so that the lateral surface 48, 64 and the projections 46, 66 contact a wall of the fissure or recess.

Altneratively or additionally, the probe is manipulating so that the lateral surface 48, 64 is oriented substantially parallel to the organic tissues and so that the distal end face is oriented substantially perpendicularly to the organic tissues immediately prior to an engaging of the organic tissues with the lateral surface 48, 64 and the projections 46, 66.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic medical probe comprising an elongate shaft provided with a head portion, said head portion having a distal end face disposed substantially in a single plane oriented at least partially transversely to a longitudinal axis of said shaft, said end face being formed with an indentation different from said end face, said indentation taking the form of at least one groove, recess, or notch extending inwardly from said end face and defined by at least two edges each formed at a respective junction with said end face, said shaft being provided with an internal longitudinal channel or bore extending to said indentation, said channel or bore having an outlet opening in said indentation, said indentation being different from said outlet opening and extending away therefrom along said end face, whereby liquid is guided from said outlet opening along said indentation and from said indentation over an extended surface of said end face relative to said channel or bore.

2. The probe defined in claim 1 wherein said head portion has a lateral surface extending generally parallel to said longitudinal axis, said lateral surface being provided with at least one outwardly or radially extending projection.

3. The probe defined in claim 2 wherein said projection is one of a plurality of substantially identical projections extending from said lateral surface.

4. The probe defined in claim 3 wherein said projections have a shape taken from the group consisting of pyramids, semi-cylinders, wedges, plates, and flaps or flattened plates.

5. The probe defined in claim 3 wherein said projections are taken from the group consisting of ridges and knurls.

6. The probe defined in claim 3 wherein said lateral surface is a perimetral surface, said projections extending circumferentially.

7. The probe defined in claim 1 wherein said head portion is enlarged in a transverse direction relative to said shaft.

8. The probe defined in claim 7 wherein said end face has an elongated shape.

9. The probe defined in claim 8 wherein said indentation is elongate and forms a groove in said end face of said head portion.

10. The probe defined in claim 1 wherein said indentation is elongate and forms a groove in said end face of said head portion.

11. The probe defined in claim 10 wherein said head portion has an elongated shape, said groove extending parallel to a length dimension of said end face.

12. The probe defined in claim 1 wherein said channel or bore is connectable to a suction source, fluid in said indentation flowing toward said channel or bore.

13. The probe defined in claim 1 wherein said channel or bore is connectable to a source of irrigation liquid, liquid in said indentation flowing away from said channel or bore.

14. The probe defined in claim 1 wherein said head portion forms a distal end portion of said shaft.

15. The probe defined in claim 1 wherein said end face is inclined or beveled relative to said longitudinal axis.

16. The probe defined in claim 1 wherein said probe head is formed separately from said elongate shaft and attached thereto.

17. An ultrasonic medical probe comprising an elongate shaft provided with a head portion, said head portion having a distal end face oriented at least partially transversely to a longitudinal axis of said shaft, said head portion having a lateral surface extending substantially parallel to said longitudinal axis, said lateral surface being provided with a plurality of outwardly or radially extending projections, said projections including overlapping rows of small plate structures a configuration of fish scales, said shaft being provided with an internal longitudinal channel or bore extending to said end face, said end face being formed with an indentation communicating with said channel or bore at a distal end thereof, said indentation extending laterally relative to said channel or bore, whereby liquid is guided over an extended surface of said end face relative to said channel or bore.

18. The probe defined in claim 17 wherein said head portion has a plurality of planar lateral faces, said projections being disposed along less than all of said lateral faces.

19. The probe defined in claim 18 wherein said projections are disposed along only one of said lateral faces.

20. The probe defined in claim 17 wherein said indentation is elongate and forms a groove in said end face of said head portion.

21. The probe defined in claim 20 wherein said head portion has an elongated shape, said groove extending parallel to a length dimension of said end face.

22. The probe defined in claim 17 wherein said head portion is enlarged in a transverse direction relative to said shaft.

23. The probe defined in claim 22 wherein said end face has an elongated shape.

24. The probe defined in claim 17 wherein said end face is inclined or beveled relative to said longitudinal axis.

25. A surgical method comprising:
providing a probe vibratable at at least one ultrasonic frequency, said probe having a distal end face disposed substantially in a single plane oriented at least partially transversely to a longitudinal axis of said shaft;
bringing said distal end face into contact with organic tissues of a patient;
during the contacting of said tissues with said distal end face, energizing said probe to vibrate said end face at said ultrasonic frequency; and
during the contacting of said tissues with said distal end face, channeling liquid between the contacted tissues and a longitudinal bore in said probe via an indentation in said end face communicating with said bore, said bore having an outlet opening in said indentation, said indentation being different from and extending away from said outlet opening, said indentation being different from said end face, said indentation taking the form of at least one groove, recess, or notch extending inwardly from said end face and defined by at least two edges each formed at a respective junction with said end face, the channeling of liquid between the contacted tissues and said bore including distributing liquid from said outlet opening along said indentation and from said indentation over said end face.

26. The method defined in claim 25, further comprising connecting said bore to a suction source, the channeling of liquid comprising guiding liquid from the contacted tissues to said bore.

27. The method defined in claim 25, further comprising connecting said bore to a source of irrigation liquid, the channeling of liquid comprising guiding liquid away from said outlet opening and along at least a portion of said end face to the contacted tissues.

28. An ultrasonic medical probe comprising an elongate shaft provided with a head portion, said head portion having a distal end face substantially disposed substantially in a single plane oriented at least partially transversely to a longitudinal axis of said shaft, said end face being formed with an indentation extending inwardly from said end face and defined by at least two edges each formed along a respective junction with said end face, said shaft being provided with an internal longitudinal channel or bore extending to said indentation, said channel or bore having an outlet opening in said indentation, whereby liquid is guided over an extended surface of said end face relative to said channel or bore.

29. The probe defined in claim 28 wherein said groove, recess or notch has a radius of curvature substantially smaller than any radius of curvature of said end face.

30. The probe defined in claim 28 wherein said groove, recess or notch takes the form of at least one groove, recess, or notch extending inwardly from said end face and defined by at least one edge formed at a junction with said end face.

* * * * *